(12) United States Patent
De Laat et al.

(10) Patent No.: US 10,307,348 B2
(45) Date of Patent: Jun. 4, 2019

(54) SINGLE LAYER TOOTH WHITENING SYSTEM

(71) Applicant: KONINKLIJKE PHILIPS N.V., Eindhoven (NL)

(72) Inventors: Antonius Wilhelmus Maria De Laat, Den Dungen (NL); James Donald Gwyer, Great Chesterford (GB); Martin John Edwards, Solihull (GB); Zeynep Sabah, Cambridge (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/545,434

(22) PCT Filed: Feb. 2, 2016

(86) PCT No.: PCT/EP2016/052100
§ 371 (c)(1),
(2) Date: Jul. 21, 2017

(87) PCT Pub. No.: WO2016/131642
PCT Pub. Date: Aug. 25, 2016

(65) Prior Publication Data
US 2018/0280259 A1  Oct. 4, 2018

(30) Foreign Application Priority Data
Feb. 17, 2015 (EP) .................................. 15155444

(51) Int. Cl.
| | |
|---|---|
| *A61K 8/04* | (2006.01) |
| *A61K 8/06* | (2006.01) |
| *A61K 8/22* | (2006.01) |
| *A61K 8/31* | (2006.01) |
| *A61K 8/42* | (2006.01) |
| *A61K 8/46* | (2006.01) |
| *A61K 8/60* | (2006.01) |
| *A61K 8/81* | (2006.01) |
| *A61K 8/90* | (2006.01) |
| *A61Q 11/00* | (2006.01) |

(52) U.S. Cl.
CPC ................ *A61K 8/044* (2013.01); *A61K 8/06* (2013.01); *A61K 8/22* (2013.01); *A61K 8/31* (2013.01); *A61K 8/42* (2013.01); *A61K 8/466* (2013.01); *A61K 8/60* (2013.01); *A61K 8/8117* (2013.01); *A61K 8/8176* (2013.01); *A61K 8/90* (2013.01); *A61Q 11/00* (2013.01)

(58) Field of Classification Search
CPC . A61K 6/02; A61K 6/087; A61K 8/19; A61K 8/24
USPC .................................. 424/49, 53; 433/217.1
See application file for complete search history.

(56) References Cited

U.S. PATENT DOCUMENTS

| | | | |
|---|---|---|---|
| 4,396,378 A * | 8/1983 | Orlowski | A61K 6/0017 106/35 |
| 5,858,332 A * | 1/1999 | Jensen | A61K 8/22 252/186.25 |
| 2005/0249677 A1 | 11/2005 | Malcmacher et al. | |
| 2005/0287084 A1 * | 12/2005 | Ibrahim | A61K 8/24 424/49 |
| 2008/0199523 A1 | 8/2008 | Finnie et al. | |
| 2009/0239983 A1 | 9/2009 | Nodera et al. | |
| 2012/0134936 A1 | 5/2012 | Kwak et al. | |
| 2012/0207793 A1 | 8/2012 | Ward et al. | |
| 2013/0245153 A1 | 9/2013 | Schwantes et al. | |

FOREIGN PATENT DOCUMENTS

| | | |
|---|---|---|
| EP | 1736135 A1 | 12/2006 |
| WO | 0101940 A1 | 1/2001 |
| WO | 03094877 A1 | 11/2003 |
| WO | 2004016237 A1 | 2/2004 |
| WO | 2005058267 A1 | 6/2005 |
| WO | 2008147997 A1 | 12/2008 |
| WO | 2013128328 A2 | 9/2013 |
| WO | 2013162404 A1 | 10/2013 |
| WO | 2015071386 A1 | 5/2015 |

OTHER PUBLICATIONS

Napper: "Polymer Solution Thermodynamics", Chapter 3 of Polymeric Stabilization of Colloidal Dispersions; Academic Press (1983).

* cited by examiner

*Primary Examiner* — Walter E Webb

(57) ABSTRACT

A varnish composition is provided comprising a hydrophilic oral care agent, such as a peroxide material, dispersed in a solution of a film-forming hydrophobic polymer in a non-polar solvent. The solvent is selected so as to be a good solvent for the polymer and to be susceptible to evaporation. The composition can be applied as a single layer varnish, preferably a whitening varnish. E.g., the dispersed hydrophilic peroxide material is an aqueous peroxide solution, such as a hydrogen peroxide solution, whereby the dispersion is an emulsion.

14 Claims, 3 Drawing Sheets

(a)

(b)

(c)

SINGLE LAYER TOOTH WHITENING SYSTEM

CROSS-REFERENCE TO PRIOR APPLICATIONS

This application is the U.S. National Phase application under 35 U.S.C. § 371 of International Application No. PCT/EP2016/052100, filed on Feb. 2, 2016, which claims the benefit of European Patent Application No.15155444.1, filed on Feb. 17, 2015. These applications are hereby incorporated by reference herein.

FIELD OF THE INVENTION

The invention relates to the dental care arts, and related arts and more specifically concerns a varnish composition and method for whitening teeth.

BACKGROUND OF THE INVENTION

Oral care agents can be applied to teeth via varnish compositions that release the agents into the teeth. Such release takes place either via water present in the formulation, or as moisture from the teeth ingresses through the inner surface of the varnish. The use of varnish compositions as a carrier for oral care agents, brings about several advantages. Particularly, applying a liquid varnish composition onto the teeth can be done easily. This is, e.g., by painting or other spreading techniques such as by using a syringe, brush, or spatula.

A particular advantage is that dental trays, or other invasive application devices, can be avoided, as a varnish composition can be painted or otherwise be manually spread onto the teeth. This is of benefit in a professional care environment, but also allows patients or users to apply such oral care composition by themselves.

However, wetting of the outer surface of the varnish can cause the oral care agents to leak into the mouth (e.g., towards the lips) in addition to into the teeth, thereby reducing the amount of oral care agent delivered to the teeth. The varnish composition may also be soft and easily washed away, thereby not allowing an effective amount of the oral care agent to be delivered to the teeth. The deposited varnish composition may also have a rough surface that can irritate the lips and other soft tissues. Furthermore, the deposited composition may have an undesirable appearance in terms of a rough surface, poor colour, and/or undesirable reflectance properties.

The foregoing issues are recognized in the art. In US 2005/0249677 A1 reference is made to a bleaching method that involves painting a bleaching composition directly onto a person's teeth. It is thereby mentioned that a perceived advantage of paint-on bleaching is that it eliminates the need for a dental tray, but that the main disadvantage of a paint-on bleaching composition is that it remains directly exposed to the person's saliva and disruptive forces found in a person's mouth. In the reference, it is foreseen to apply a dental bleaching composition onto the teeth, applying a protective composition on or adjacent to gingival tissue, and placing a moisture-resistant barrier layer over the tooth surface to be bleached. The barrier layer is a shaped device, e.g., in the form of a dental tray, sheet, strip, or patch. Therewith, i.e., by providing a shaped device to be placed in the mouth, the reference largely reduces, if not altogether diminishes, the advantages associated with applying the oral care agent via a composition that can be painted onto the teeth.

Further, a dual layer whitening varnish is available under the trade name Philips Zoom QuickPro product. This is typically used in a short, five-minute dental office procedure. The product is based on a two-layer technology with a 20% hydrogen peroxide whitening varnish followed by a sealant layer that dries in seconds and locks the hydrogen peroxide layer into place. Whilst this product provides a considerable advancement in teeth whitening technology, it would be desired for some applications, e.g. to further facilitate domestic use, to provide a single layer varnish.

It is desired to provide a system and method are which can overcome some of the problems with systems as existing prior to the aforementioned QuickPro product, such as having a reduced leakage rate of an oral care agent into a mouth, but which is fully based on a varnish-type composition. I.e., a system is sought that is entirely based on compositions that can be easily applied onto tooth surfaces as a fluid, and which are thereafter cured.

SUMMARY OF THE INVENTION

In order to better address the foregoing desires, the invention, in one aspect, presents an oral care varnish composition comprising a dispersion of a hydrophilic oral care agent in a solution of a film-forming hydrophobic polymer in a non-polar solvent, said solvent being volatile and being characterized as a better than theta ($\theta$) solvent for the polymer.

In another aspect, the invention provides a cured varnish composition on at least one tooth, obtainable by applying on said at least one tooth a varnish composition comprising a dispersion of a hydrophilic oral care agent in a solution of a film-forming hydrophobic polymer in a non-polar solvent, said solvent being volatile and being characterized as a better than theta ($\theta$) solvent for the polymer, and curing said composition by evaporation of solvent; said cured composition comprising a hydrophilic oral care agent dispersed in a matrix of a hydrophobic polymer, wherein the hydrophilic oral care agent is present in an aggregate state at least at the surface of the cured composition facing the tooth, and a layer of the hydrophobic polymer is present at least at the surface of the cured composition facing away from the tooth.

In yet another aspect, the invention is a method of applying an oral care agent to teeth, the method comprising providing a varnish composition comprising a dispersion of a hydrophilic oral care agent in a solution of a film-forming hydrophobic polymer in a non-polar solvent, said solvent being volatile and being characterized as a better than theta ($\theta$) solvent for the polymer, applying at least one layer of the composition to at least one tooth, and allowing the solvent to evaporate so as to cure the varnish composition.

DETAILED DESCRIPTION OF THE EMBODIMENTS

Figure 1:
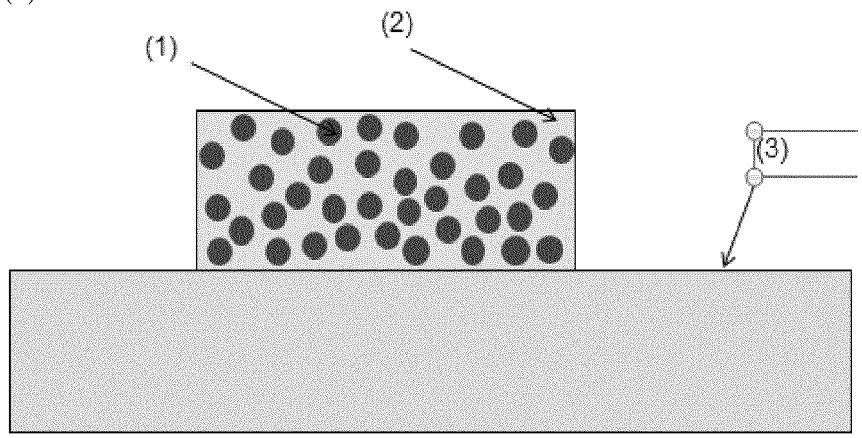
FIGS. 1 (a)-(c) is a schematic representation of the concept of the invention, with aqueous peroxide emulsified in a hydrophobic polymer solution.
Figure 1:
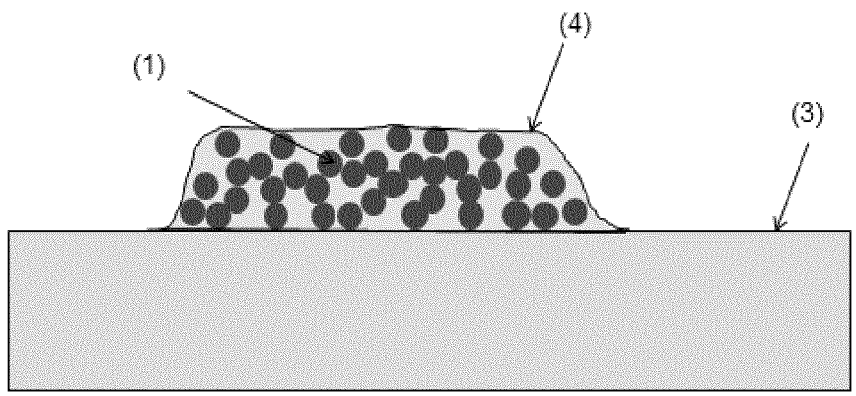
Figure 1:
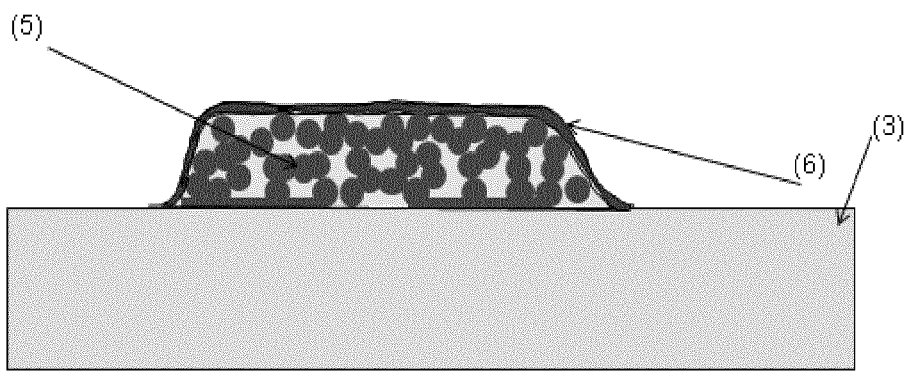

The invention makes it possible to retain hydrophilic oral care agents, such as a hydrophilic peroxide material, on teeth, without having to apply a separate barrier. According to the invention, a layer of the varnish composition is applied onto teeth, and then dried (cured) by allowing the solvent to evaporate. The invention works for both suspended oral care agents, such as solid peroxides, and emulsions of aqueous oral care agents, such as aqueous hydrogen peroxide solutions.

The invention pertains to hydrophilic oral care agents. Such agents are either present in the form of aqueous solutions, or in the form of hydrophilic particles. Representative examples of such aqueous solutions include solutions of hydrogen peroxide in water, in various possible different concentrations. Representative examples of hydrophilic particles include solid peroxides, such as carbamide peroxide and polyvinylpyrrolidone hydrogen peroxide adduct. Other examples of hydrophilic oral care agents include other oral care agents that are intended to go into the tooth (e.g. remineralisation agents, fluoride agents, desensitizing agents).

The composition of the invention comprises a solution of a film-forming polymer in a volatile solvent. As the solvent evaporates, the composition of the invention results in the formation of a polymer film at the side where the evaporation takes place (i.e., facing away from the teeth). This polymer film serves to close-off (seal) the hydrophilic active agent from the aqueous outside environment of the mouth. Without wishing to be bound by theory, the inventors believe that the following explanation can be given.

The hydrophobic polymer and the non-polar volatile solvent both are of a different phase than the dispersed hydrophilic agent. Upon evaporation of solvent at the surface of an applied composition, non-polar solvent will migrate towards the surface dragging along both the hydrophobic polymer and the dispersed hydrophilic agent. Due to the hydrophobic nature of the surface the dispersed hydrophilic agent will be depleted from of this region. At the same time the concentration of the hydrophobic polymer increases due to the evaporation of the solvent and starts to form a solid polymer film. This has a dual effect, viz. to further enhance the sealing of the agent from the aqueous environment of the mouth, and to effectively increase the concentration of the agent where it is needed, viz. on the teeth.

The solvent is required to be non-polar, and to be a good solvent for the hydrophobic polymer. Good solvents are those where the solute-solvent interaction is more favourable than the solute-solute interaction. This refers to the so-called theta ($\theta$) condition. According to accepted theory, polymer chain conformation is affected by solvent quality. The intermolecular interactions between polymer chain segments and coordinated solvent molecules have an associated energy of interaction which can be positive or negative. For a good solvent, interactions between polymer segments and solvent molecules are energetically favourable, and will cause polymer coils to expand. For a poor solvent, polymer-polymer self-interactions are preferred, and the polymer coils will contract. The quality of the solvent depends on both the chemical compositions of the polymer and solvent molecules and the solution temperature. If a solvent is precisely poor enough to cancel the effects of excluded volume expansion, the theta ($\theta$) condition is satisfied. For a given polymer-solvent pair, the theta condition is satisfied at a certain temperature, called the theta ($\theta$) temperature or theta point. A solvent at this temperature is called a theta solvent. In the event of dissolving a polymer, in a good (better than $\theta$) solvent the interactions between polymer segments and solvent molecules will cause polymer coils to expand. The polymer chains will adopt a configuration that is known as a self-avoiding random walk. The resulting chain expansion promotes the formation of a closed film.

The $\theta$-point can be determined by methods known in the art. Particularly, the $\theta$-point can be determined by light scattering or osmotic pressure measurements, such as mentioned in Donald H. Napper, Polymeric Stabilization of Collodial Dispersions, Academic Press (1983), Chapter 3 "Polymer Solution Thermodynamics" with particular reference to section 3.2.7.2 on page 43 ("Determination of the theta-point"). For the purpose of the present invention, a rapid method can be applied. This includes the methods referred to that are based on measuring the temperature of phase separation over a range of polymer concentrations. Particularly, theta can be determined by measuring the temperature of phase separation over a range of volume fractions $v_2$ of the polymer in the solvent, $10^{-5} \leq v_2 \leq 10^{-2}$. This yields data to generate a plot of the reciprocal temperature versus the logarithm of the volume fraction of polymer. Extrapolation to log $v_2$=0 yields the value of $1/\theta$.

Preferably, the film-forming polymer and the non-polar volatile solvent are chosen such as to result in a desirably non-porous polymer film. It will be understood that the better closed-off the film is, the better the hydrophilic oral care agent remains available to exert its action on the teeth.

Particularly, according to the invention it is preferred to choose a polymer and solvent combination that satisfies the following test (KI test):

- A thin layer (100-200 micron) of varnish is applied on a substrate (e.g. a glass plate)
- The solvent is allowed to evaporate at conditions mimicking the oral situation (ambient to slightly elevated temperature)
- After evaporation is completed a few drops of a test liquid are placed on the surface of the dried varnish layer
- The test liquid is a colourless aqueous solution (0.5 M) of KI. In contact with hydrogen peroxide $I_2$ ($I_3^-$) is formed which has a deep brown colour. The level of coloration is a qualitative indication of the leakage of hydrogen peroxide through the surface film.
- after 30 minutes standing, it is assessed by visual inspection whether the droplet has become coloured;
- an at most moderate (light brown) discoloration indicates that the polymer/solvent combination provides a sufficient barrier.

Release to the tooth can be tested with the same test liquid in adapted way.

After application and curing, the dried layer is peeled from the substrate and inverted. Subsequently, the KI test liquid is applied on the surface of the dried film that should release the hydrogen peroxide to the tooth.

A fast and strong brown coloration indicated good release of peroxide towards the tooth.

A large difference in colour development on both sides of the cured layer demonstrates the principle of the invention.

It is noted that the foregoing test is conducted with peroxide, since this provides such a clear discoloration by the reaction with KI. Evidently, the result of this simple and straightforward test is representative for any hydrophilic oral care agent.

Once having been apprised of the present invention, the skilled person will be able to apply technical considerations that are known from the field of coatings. This refers to, inter alia, settings such as the concentration of the polymer and the active agent.

In coating technology the properties of dried layers (films) are frequently related to the pigment volume concentration (PVC). At low PVC, there is a polymer film with some scattered pigment particles. At high PVC, a dried film may result that comprises a packed (but generally porous) layer of particles with only a minor amount of polymer present. A parameter known from coatings technology is therefore the so-called "critical PVC (CPVC)". This is the ratio where the voids between the particles are just completely filled by polymer. In the composition of the invention, the counterpart of the pigment in a coating composition, will be the oral care agent. The skilled person will be able to determine the "CPVC" for the dispersed volume of the oral care agent (dispersed particles or droplets) as well. In the compositions of the invention, it is recommended to provide a ratio of polymer to oral care agent such that, by analogy, the composition has a "PVC" greater than said "CPVC." This is believed to promote that the droplets of the aqueous phase are driven into contact with each other and the surface upon evaporation.

As further guidance, the foregoing is illustrated in Table 1 below, with reference to an example composition in accordance with the invention.

TABLE 1

|  | Isopar E | Isodecane | Emulsifier | Aqueous phase | Polymer (Kraton FG) |
|---|---|---|---|---|---|
| Wt. % | 31.55 | 1.59 | 0.38 | 63.61 | 2.87 |
| Density (g/cm$^3$) | 0.76 | 0.77 | 0.8 | 1.08 | 0.91 |

The volume fraction of droplets in the composition is: 63.6/1.08/(63.6/1.08+0.38/0.8+2.87/0.91+1.59/0.77+31.55/0.76=0.56 In the cured layer PVC is 63.6/1.08/(63.6/1.08+0.38/0.8+2.87/0.91+1.59/0.77=0.91.

Without wishing to be bound by theory, the inventors believe that the principles of the invention can be further explained as follows. Whilst the explanation is given, by way of example, for solid peroxides and for aqueous peroxide solutions, it extends to other hydrophilic oral care agents.

Upon drying (curing), the solid particles will flocculate. They will touch each other and the dental surface, whilst remaining unchanged as particles. Upon water ingression, the particles will start to decompose and release peroxide (which as such is a well-established principle). In the event of aqueous peroxide solutions, the varnish is an emulsion with small liquid droplets containing the peroxide. Upon drying the droplets will also touch each other initially. However, different from the aforementioned solid peroxides, these droplets can also coalesce (flow together) or spread on the surface of the tooth. In the event of emulsions enough water is present in the formulation itself, so there is no need for water from the tooth to start the release of peroxide.

In both cases, the peroxide is enclosed and screened from the environment by a hydrophobic material. For, after drying by solvent evaporation, a layer of the hydrophobic polymer is present on the surface of the cured varnish composition facing away from the teeth. In both cases, the hydrophilic peroxide material originally dispersed (suspended or emulsified) in the hydrophobic polymer solution forms an aggregate at least at the surface of the cured composition facing the teeth. Depending on the uncured state of the varnish composition, viz. suspension or an emulsion, the aggregate comprises particles that have clustered together or droplets that have coalesced together.

In connection herewith, the invention also resides in a cured varnish composition on at least one tooth, said cured composition being obtainable by applying a varnish composition according to the invention on said at least one tooth, and curing said composition by evaporation of solvent. The resulting cured composition still comprises a hydrophilic oral care agent, such as a peroxide material, dispersed in a matrix of a hydrophobic polymer. However, as a result of the curing process, and as a result of the aqueous environment at the surface of the at least one tooth, a difference occurs in the cured composition at the side facing the tooth, and at the side facing away from the tooth. In accordance with the invention, the hydrophilic oral care agent, such as a peroxide material, is present in an aggregate state, as explained above, at least at the surface of the cured composition facing the tooth. A layer of the hydrophobic polymer is present at least the surface of the cured composition facing away from the tooth.

The concept of the invention is schematically illustrated in FIG. 1.

The invention pertains to applying a hydrophilic oral care agent, such as a hydrophilic peroxide material. Examples of peroxides for use as whitening agents (also known as "bleaching agents") in the varnish composition of the invention include, but are not limited to, hydrogen peroxide, carbamide peroxide, polyvinylpyrrolidone hydrogen peroxide adduct and other hydrogen peroxide complexes, alkali metal percarbonates, perborates, such as sodium perborate, persulfates, such as potassium persulfate, calcium peroxide, zinc peroxide, magnesium peroxide, strontium peroxide, peroxyacids, and combinations thereof. This refers to an aqueous, or otherwise polar, liquid or solid comprising a peroxide. Non-limiting examples thereof include a solution of hydrogen peroxide in water, carbamide peroxide, or complexes of PVP and hydrogen peroxide.

The hydrophilic oral care agent is dispersed in a solution of a hydrophobic film-forming polymer in a volatile non-polar solvent. It will be understood that in the event of a liquid oral care agent, the dispersion takes the form of an emulsion of finely divided droplets of the oral care agent in the solvent. In the event of a solid oral care agent, the dispersion will take the form of a suspension of finely divided particles in the solvent.

For teeth whitening applications, the varnish composition will comprise a bleaching agent. It will be understood that the bleaching agent used herein can be compounds which are themselves bleaches and compounds which are bleach precursors, such as carbamide peroxide, which react or decompose to form a bleach, such as hydrogen peroxide. The bleaching agents can be solid or liquid at ambient conditions. Liquid bleaching agents include peroxides such as hydrogen peroxide, in aqueous solution. Solid bleaching agents include carbamide peroxide, which is an adduct (or stable mixture) of urea and hydrogen peroxide ($CH_4N_2O$—$H_2O_2$). The material is a white, crystalline solid that dissolves in water to release the two components from which it is formed. Carbamide peroxide contains the equivalent of 36.1 wt. % hydrogen peroxide. For example, a varnish composition containing 16.6 wt. % carbamide peroxide can release 5.9 wt. % hydrogen peroxide. Solid bleaching agents can be introduced in the form of particles, whereby the particles are hydrophilic.

The hydrogen peroxide (or its precursor) may be present in the varnish composition in an amount sufficient to provide hydrogen peroxide in the layer applied to the teeth, when uncured, generally in an amount of from 0.1 wt. % to 50 wt. %, and particularly at a concentration so as to provide an amount of peroxide equivalent to at least 1 wt. % up to 35 wt. % hydrogen peroxide, preferably from 2 wt. % to 25 wt.

%. Typical concentrations are 2-8 wt. %, particularly for domestic use, or 20-25 wt. %, particularly for application by a dental professional. It will be understood that in the event of aqueous emulsions of hydrogen peroxide, the concentration of the peroxide in the aqueous emulsion droplets will necessarily be higher than the desired concentration in the overall composition.

Preferably, the oral care agent is a liquid. More preferably, in the event of use in teeth whitening, it is an aqueous solution of hydrogen peroxide.

The polymer acts as a binder for the varnish, after curing through evaporation of the solvent. The polymer is film-forming, preferably to the extent that it forms non-porous, closed film upon solvent evaporation at he evaporating surface, in order to form a layer on the teeth to be whitened. The polymer further is hydrophobic, in order for it to act as a barrier for the hydrophilic oral care agent and the saliva. Hydrophobic polymers are generally characterized by their tendency of not mixing with water, and preferably repelling water. The classification of a polymer as being either hydrophobic or hydrophilic is well-known to the skilled person, and is frequently used in the art.

The viscosity of the composition of the invention can vary in a wide range from just above the solvent viscosity (generally below 1 mPas) to over 1000 mPas.

Suitable film-forming, hydrophobic polymers are, for example, polymers as can be found in cosmetics e.g. water proof or water resistant sun screens, kiss-proof lipsticks, and nail polishes. The skilled person is fully aware of the types of polymers used in the foregoing applications, and will be able to use same in the varnish composition of the present invention.

Examples of hydrophobic polymers include, but are not limited to: hydrogenated polyisobutene, Ethylene/Propylene/Styrene Copolymer, Butylene/Ethylene/Styrene Copolymer (Penreco), alkylated polyvinylpyrrolidone (e.g. ex Ashland),poly alpha olefins (e.g. ex New Phase Technologies), Hydrogenated Polycyclopentadiene (e.g. ex Kobo), Polyvinylstearylether (e.g. ex Phoenix Chemicals), or polystyrene/rubber block-copolymers as sold under the trade name Kraton.

Copolymers including polystyrene end blocks and mid-blocks of polyisoprene or polybutadiene are commercially available under the trade name Kraton® D. Copolymers including polystyrene end blocks and poly(ethylene-butylene) or poly(ethylene-propylene) mid-blocks are commercially available under the trade name Kraton® G.

Exemplary polystyrene-based copolymers include those available under the trade names Kraton® FG1901 and Kraton® G1652. The Kraton® FG1901 material is a clear, linear triblock copolymer based on styrene and ethylene/butadiene with a styrene content of about 30%. The Kraton® G1652 material is a clear or translucent linear triblock copolymer based on styrene and ethylene/butylene (SEBS) with a styrene/rubber ratio of 30/70. Kraton FG polymers are SEBS polymers with maleic anhydride (MA) grafted onto the rubber midblock. The commercial Kraton FG polymers have 1.0 to 1.7 wt. % MA grafted onto the block copolymer. Preferred formulations are with Kraton FG1901GT (a linear triblock copolymer based on styrene and ethylene/butylene with a polystyrene content of 30%), G1701E (a linear diblock copolymer based on styrene and ethylene/propylene, with bound styrene of 35% mass), and A1536HU (linear triblock copolymer based on styrene and ethylene/butylene, provided as an undusted powder).

The concentration of the polymer in the composition is generally from 0.1 wt. % to 80 wt. % depending on the properties of the dissolved polymer/solvent system, for the Kratons currently used preferably of from 0.5 wt. % to 15 wt. %. The composition can further comprise adjuvants and additives, such as emulsifiers, film-forming agents (the hydrophobic polymers), lubricants, emollients, thickeners, fillers, evaporation control agents, enhancers for film formation, and the like.

Also, the varnish composition can comprise additional oral care agents and/or other additives.

The varnish composition of the invention comprises one or more additional oral care agents.

Preferred are bleaching (whitening) agents as discussed above. Other hydrophilic agents suitable for use in the compositions of the invention are, e.g., selected from the group consisting of remineralising agents, anti-caries agents, anti-plaque agents, anti-odour agents, fluoride agents, antibacterial agents, biofilm preventing or dispersing agents, pH regulating agents, long-term protective components, reactive enzymes, reactive radicals, and combinations thereof. In an interesting embodiment, one or more of the aforementioned agents are present in addition to whitening agents.

Specific examples of oral care agents include:

Tartar control (anticalculus) agents: these may include phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts, and mixtures thereof.

Fluoride ion sources: These may be useful, for example, as an anti-caries agent. Orally acceptable fluoride ion source which can be used include potassium, sodium and ammonium fluorides and monofluorophosphates, stannous fluoride, indium fluoride and mixtures thereof.

Tooth and soft tissue desensitizers: these may include stannous ions, such as halides and carboxylate salts, arginine, potassium citrate, potassium chloride, potassium tartrate, potassium bicarbonate, potassium oxalate, potassium nitrate, strontium salts, and mixtures thereof.

Antimicrobial (e.g., antibacterial) agents: these may include orally acceptable antimicrobial agents, such as Triclosan (5-chloro-2-(2,4-dichlorophenoxy)phenol); 8-hydroxyquinoline and salts thereof, zinc and stannous ion sources such as zinc citrate; copper (II) compounds such as copper (II) chloride, fluoride, sulfate and hydroxide; phthalic acid and salts thereof such as magnesium monopotassium phthalate; sanguinarine; quaternary ammonium compounds, such as alkylpyridinium chlorides (e.g., cetylpyridinium chloride (CPC), combinations of CPC with zinc and/or enzymes, tetradecylpyridinium chloride, and N-tetradecyl-4-ethylpyridinium chloride); bisguanides, such as chlorhexidine digluconate; halogenated bisphenolic compounds, such as 2,2' methylenebis-(4-chloro-6-bromophenol); benzalkonium chloride; salicylanilide, domiphen bromide; iodine; sulfonamides; bisbiguanides; phenolics; piperidino derivatives such as delmopinol and octapinol; *magnolia* extract; grapeseed extract; thymol; eugenol; menthol; geraniol; carvacrol; citral; eucalyptol; catechol; 4-allylcatechol; hexyl resorcinol; methyl salicylate; antibiotics such as augmentin, amoxicillin, tetracycline, doxycycline, minocycline, metronidazole, neomycin, kanamycin and clindamycin; and mixtures thereof. Other useful antimicrobials are disclosed in U.S. Pat. No. 5,776,435.

Antioxidants: orally acceptable antioxidants which can be used include butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

Antiplaque (e.g., plaque disrupting) agent: orally acceptable antiplaque agents can include stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates, and mixtures thereof.

Anti-caries agents: examples of these include calcium glycerylphosphate and sodium trimetaphosphate.

Anti-inflammatory agents: orally acceptable anti-inflammatory agents can include steroidal agents, such as flucinolone and hydrocortisone, and nonsteroidal agents (NSAIDs) such as ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone, phenylbutazone, and mixtures thereof.

$H_2$ antagonists: antagonists useful herein include cimetidine, etintidine, ranitidine, ICIA-5165, tiotidine, ORF-17578, lupititidine, donetidine, famotidine, roxatidine, pifatidine, lamtidine, BL-6548, BMY-25271, zaltidine, nizatidine, mifentidine, BMY-52368, SKF-94482, BL-6341A, ICI-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728, HB-408.4, and mixtures thereof.

Nutrients: Suitable nutrients include vitamins, minerals, amino acids, proteins, and mixtures thereof.

Preferred hydrophilic oral care agents, besides the peroxide materials mentioned previously, include sodium fluoride, ACP (amorphous calcium phosphate, including the calcium and phosphate precursors thereof), potassium nitrate, potassium oxalate, phosphates and polyphosphates, mono fluorphosphate, aminfluoride, xylitol, chlorhexidine (CHX), cetylpyridiniumchloride (CPC), triclosan (Irgasan), stannous fluoride (SnF2), zinc acetate, silver diamine fluoride, hypochlorite, chlorine dioxide, iodine.

In an interesting embodiment, the composition of the invention comprises at least one oral care agent selected from the group consisting of hydrogen peroxide, sodium fluoride, ACP, potassium nitrate, potassium oxalate, CHX, and CPC.

As examples of other additives, the varnish composition may include one or more of the following:

Colorants: The colorant may be selected to provide the film with a white appearance or a tint.

Tooth and soft tissue desensitizers: these may include stannous ions, such as halides and carboxylate salts, arginine, potassium citrate, potassium chloride, potassium tartrate, potassium bicarbonate, potassium oxalate, potassium nitrate, strontium salts, and mixtures thereof.

Anti-staining agents: such as silicone polymers.

Flavouring agents: any of the flavouring agents commonly used in toothpastes may be used, by way of example.

Other possible additives include thermochromics and colour-changing additives. These types of additives may enable a user to visually determine when a treatment is complete.

The additional agents and additives, if present, can be present in amounts generally known to the skilled person. A typical ranges is of from 0.5 wt. % to 10 wt. %, particularly of from 2 wt. % to 5 wt. %.

The solvent in which the hydrophilic oral care agent, such as a peroxide material, is dispersed, has two main functions. One is to dissolve a binder for the varnish. The other is to be capable of evaporation, so as to cure the varnish by allowing it to solidify. Since the binder in the varnish composition of the invention is a hydrophobic polymer, the solvent is selected to be non-polar, as further explained below. Since the solidification of the varnish should occur by solvent removal from the composition when same has been applied onto teeth, the removal can occur with or without heating. Preferably evaporation is at ambient temperature or slightly above (generally 15° C. to 50° C.). Evaporation is a type of vaporization of a liquid that occurs from the surface of a liquid into a gaseous phase that is not saturated with the evaporating substance. To this end, the solvent preferably is a volatile solvent, as further explained below. Blowing of air can be used to stimulate evaporation.

In an interesting embodiment, formulations can be used that are stiff gels at room temperature, but fluid at elevated temperature (warm water temperature, e.g. 40° C. to 60° C., typically about 50° C.). Such formulations will be applied with heating to the temperature mentioned, and solvent evaporation will then also conveniently occur at such temperature.

Solvents can be broadly classified into two categories: polar and non-polar. The polarity of solvents, mixtures thereof, and mixtures of solvents and water, can be generally determined on the basis of the dielectric constant of the solvent or solvent mixture. Water, which is highly polar, is indicated, at 0° C., by a dielectric constant of 88. Solvents with a dielectric constant of less than 15 are generally considered to be nonpolar.

The volatility of a solvent is dependent on its boiling point and its vapour pressure. Solvents having a low boiling point and a high vapour pressure at ambient temperature, will generally be volatile. A low boiling point generally means below the boiling point of water (100° C. at 1 atm.). The vapour pressure of a liquid is the pressure of a vapour in equilibrium with the liquid phase. Evaporation tends to proceed more quickly in liquids with higher vapour pressure. Preferably, solvents are chosen that have not such a high volatility that the varnish composition cannot be packaged without measures to prevent the solvent from untimely evaporation from the package. The skilled person will be capable of adjusting the evaporation rate of a solvent as necessary, by adding one or more further solvents to reduce or increase the evaporation rate.

In general, a volatile solvent as used in the invention will have a boiling near that of water, and a vapour pressure near that of water. Curing times, determined by the rate of evaporation of the solvent, will generally be between 10 seconds and 10 minutes. Longer times are conceivable but will generally be considered to be less acceptable by persons using it. Preferred curing times are of from 20 seconds to 2 minutes, and in a particular preference the solvent is capable of evaporation at a rate at least comparable to that of ethanol, so as to bring about a curing time of about 30 seconds.

Preferred solvents include alkanes, isoalkanes, isoparaffins, siloxanes, fluorinated hydrocarbons, and mixtures of these solvents.

It will be understood that the solvents used in the present invention should be selected from those solvents that are acceptable for oral use. Whilst the full possible selection of such solvents may differ depending on regulatory insights, the skilled person will have no difficulty known which solvents are acceptable.

Exemplary solvents have the general formula: $C_nH_{2+1}C_mH_{2m+1}$ where n and m are independently greater than or equal to 1 and smaller than 9, or smaller than 5, and n+m <12 or <8. The solvent may be, for example, a $C_4$-$C_{12}$ branched or unbranched alkane such as pentane, isopentane, heptane, isoheptane, octane, isooctane, a fluorinated solvent, cyclomethicone, and combinations thereof. In specific embodiments, the solvent may be selected from the group consisting of heptane, pentane, and mixtures thereof.

Examples of solvents include those listed in Table 2 below. Alkanes form a very interesting embodiment, with heptane and isooctane being preferred. In an interesting embodiment, isopentane is included in a solvent mixture to reduce cure time. Isoparaffin is a technically attractive alternative to the alkanes. These are widely used in cosmetics and have a tendency to be better accepted by consumers.

TABLE 2

| Solvent | Boiling Point (° C.) | Vapour pressure (kPa) at 20° C. |
| --- | --- | --- |
| Pentane | 36 | 57.90 |
| Isopentane | 28 | 76.99 |
| Heptane | 98 | 5.33 |
| Isooctane | 99.3 | 5.5 |
| Isododecane | 209 | <0.1 |
| Cyclomethicone (D4) | 175 | 0.09 |
| Cyclomethicone (D5) | 210 | 0.019 |
| C7-8 Isoparaffin | 110-125 | <3.1 |
| C8-9 Isoparaffin | 130-165 | <1.0 |

The varnish composition of the invention preferably comprises one or more emulsifiers so as to aid the formation of a stable water-in-oil (w/o) emulsion in the event of a liquid peroxide material. Suitable emulsifiers include, but are not limited to sorbitan fatty esters such sorbitan monolaurate (Span 20), sorbitan monostearate (Span 60), sorbitan monooleate (Span 80), sorbitan sesquioleate (Span 83), sorbitan isostearate (Span 120), sodium dioctyl sulfosuccinate (Aerosol OT100), but also polymeric surfactants such as Hypermer B261 or mixed emulsifiers such as Arlacel 1690 (Sorbitan isostearate with polyglyceryl-3 polyricinoleate).

The invention also pertains to a method is provided of applying a hydrophilic oral care agent, such as a tooth whitening agent, to teeth, the method comprising providing a varnish composition as described hereinbefore, in all of its embodiments to at least one tooth, and allowing the solvent to evaporate so as to cure the varnish composition.

In a preferred method of applying a hydrophilic oral care agent, the oral care agent is a peroxide and the method is a teeth whitening method.

The varnish composition is applied to the teeth of a person or animal to be treated. The composition may be applied by a dental professional, such as a dentist, or by the wearer. For example, the composition may be applied to the teeth using an applicator, such as a pen, brush, piece of foam, cloth applicator, dental tray, or to two-compartment syringe to form the first layer. In other embodiments, the composition may be inserted into an applicator, such as into the dental tray, which is positioned adjacent the teeth and then removed, for example, after partial drying/curing of the composition.

The composition may be applied to the teeth at a thickness of, for example, from 25-500 µm, such as from 50-300 µm, e.g., about 100 µm. In some embodiments wherein the hydrophilic peroxide material is present in the form of particles, the film is greater in thickness than the average diameter of the particle, for example, at least twice or at least three times the average diameter of the particles. This allows the varnish to be smooth to the touch, when cured.

After sufficient time to effect treatment with the hydrophilic oral care agent, such as a bleaching agent, the varnish layer is removed. At the end of the treatment period, the layer is removed from the teeth by, for example, peeling it away from the teeth and/or by brushing the teeth. The process may be repeated, for example, once a day, week, or month or more or less frequently.

In the event of teeth whitening, the treatment period can refer to a period of time sufficient to effect at least a partial whitening of the teeth, e.g., a change in colour of at least 1 ΔE. ΔE is computed according to the 1976 definition by the International Commission on Illumination (CIE76), using the L*,a,*b* values of the teeth (which may be averaged values), before whitening (denoted by the subscript 1) and after whitening (denoted by the subscript 2), according to the formula:

$$\Delta E = \sqrt{(L_2^* - L_1^*)^2 + (a_2^* - a_1^*)^2 + (b_2^* - b_1^*)^2}.$$ Said L*,a,*b* values are known in the art.

In this respect, the invention also pertains to a method of whitening teeth of a subject, more particularly a human subject, the method comprising applying a varnish composition as described hereinbefore, in all of its embodiments, to at least one tooth of said subject, allowing the solvent to evaporate so as to form a cured varnish layer, and allowing the cured varnish layer to stay on said at least one tooth for a desired treatment period. Preferably, the treatment period is of sufficient length so as to bring about a change in colour of at least 1 ΔE as defined above. Preferably, after the treatment period the cured varnish layer is removed from the teeth. It will be understood that the whitening method is a cosmetic method.

The invention further pertains to a method of making a varnish composition as described hereinbefore, in a preferred embodiment in which the hydrophilic oral care agent is a bleaching agent. The method comprises the steps of emulsifying an aqueous peroxide solution in a non-polar solvent and mixing the emulsion with a solution of a hydrophobic, film-forming polymer in a non-polar solvent. The possible peroxides, polymers, and solvents, are as described hereinbefore. Hereby the non-polar solvents can be single solvents or mixtures of solvent, and can be same or different. For both the peroxide emulsion and the polymer solution a single solvent can be used. Preferred solvents are isoparaffins, which are mixtures. More preferably, the solvent (including mixtures of solvents) for both the peroxide emulsion and the polymer solution is the same.

While the invention has been illustrated and described in detail in the drawings and foregoing description, such illustration and description are to be considered illustrative or exemplary and not restrictive; the invention is not limited to the disclosed embodiments.

For example, it is possible to operate the invention in an embodiment wherein a plurality of oral care agents is present in the composition, and the composition thereby will have more than one oral care function (e.g. combining whitening with one or more treatments such as remineralisation, fluoride treatment, or desensitization).

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain features of the invention are recited in mutually different dependent claims does not indicate that a combination of these features cannot be used to advantage. Any reference signs in the claims should not be construed as limiting the scope.

In sum the invention relates to, inter alia, a varnish composition comprising a hydrophilic oral care agent, such as a peroxide material, dispersed in a solution of a film-forming hydrophobic polymer in a non-polar solvent. The solvent is selected so as to be a good solvent for the polymer and to be susceptible to evaporation. The composition can be applied as a single layer varnish, preferably a whitening varnish. E.g., the dispersed hydrophilic peroxide material is an aqueous peroxide solution, such as a hydrogen peroxide solution, whereby the dispersion is an emulsion.

The invention is hereinafter illustrated with reference to the following examples and the figures. The examples and figures are not intended to limit the scope of the invention.

In FIGS. 1 (a-c) the concept of the invention is schematically shown. The references signs have the following meanings (described for hydrogen peroxide, but generally applicable to other hydrophilic oral care agents):
(1) Emulsion droplets with aqueous $H_2O_2$;
(2) Organic solvent with dissolved hydrophobic polymer;
(3) Tooth;
(4) Drying solution of hydrophobic polymer;
(5) Coalesced aqueous droplets containing $H_2O_2$;
(6) Hydrophobic polymer layer resulting after drying.

In FIG. 1 (a) a non-cured varnish layer is shown, applied on a tooth. In FIG. 1 (b) the state of the varnish shown during drying, with emulsion droplets coalescing. In FIG. 1 (c) the result is shown after drying, whereby coalesced emulsion droplets are shown forming a layer on the tooth, and the cured polymer forms a hydrophobic protection layer on the surface of the cured varnish layer.

EXAMPLE 1

Varnish Composition in Isoparaffin

Highly concentrated emulsions are made, as to reduce the peroxide content in the droplet. To this end 15 grams of diluted hydrogen peroxide (10-25 wt %) are emulsified in 2.5 grams of 3.3 wt. % Span 83 (emulsifier) solution in Isopar E ($C_{7-10}$ isoalkanes mixture) using an Ultra-Turrax® homogenizer.

In the next step the emulsion is mixed with a concentrated Kraton solution in isopar E to make the varnish. To this end 3 grams of the concentrated emulsion is mixed with 0.6 grams of 13 wt % Kraton FG1901GT in Isopar™ E. About 0.6 grams of Isopar™ E is added to adjust the viscosity.

In another sample, 3 grams of concentrated emulsion is mixed with 2 grams of 5.5 wt % Kraton G1701E in Isopar™ E. To facilitate mixing, the varnish is heated to 40-60° C.

EXAMPLE 2

Varnish Composition in Heptane

In the first step, 0.75 grams of aqueous hydrogen peroxide (HP) is emulsified in heptane. The HP solution is added to 3 grams of a 1-5 wt. % solution of emulsifier in heptane. The emulsification is done with a high shear impeller, viz. a Turrax® T25. Secondly, 1 gram of emulsion is mixed with 1 gram of a 10 wt. % Kraton FG1901 solution in heptane. After careful mixing, the varnish is ready for use. Similarly, other varnish compositions are made using Kraton FG1901 in heptane. An overview of the compositions of Example 2 is given in Table 3 below.

TABLE 3

| Sample Emulsifier | Composition (% wt) | | | |
|---|---|---|---|---|
| | Heptane | $H_2O_2$ (aq) | Kraton | Emulsifier |
| Span 60 | 84.1 | 9.9 | 5.0 | 1.0 |
| Span 20 | 81.5 | 12.2 | 3.7 | 2.5 |
| Span 80 | 85.1 | 8.9 | 5.0 | 1.0 |
| Aerosol OT100 | 82.7 | 10.4 | 4.9 | 2.0 |
| Hypermer B261 | 85.2 | 9.0 | 5.0 | 0.8 |
| Span 120 | 83.8 | 9.0 | 5.2 | 2.0 |
| Span 83 | 83.9 | 9.0 | 5.0 | 2.0 |
| Arlacel 1690 | 83.9 | 8.9 | 5.3 | 1.9 |

EXAMPLE 3

Varnish Composition with Different Polymers

Similar to Example 1, other varnish compositions are made in isoparaffin (Isopar™ E). The emulsifier is Span 83. These compositions are summarized in Table 4 below.

TABLE 4

| Binder (%) | % Span 83 | % Solvent | % Aqueous Phase | HP % in emulsion (% in bottle) |
|---|---|---|---|---|
| Kraton G1701E (2.11) | 0.29 | 44.56 | 53.0 | 15.0 (8.0) |
| Kraton FG1901GT (1.84) | 0.33 | 36.33 | 61.5 | 15.0 (9.2) |
| Kraton A1536HU (0.62) | 0.42 | 20.88 | 78.1 | 10.0 (7.8) |

EXAMPLE 4

Test of Protection and Release

A thin layer of varnish is coated on glass and also on a foil surface from which it can be easily removed after drying. A suitable foil is a liner as used for adhesive films. The liner may be additionally coated with a thin layer of hydrophilic polymer such as polyethylene glycol to mimic the hydrophilic tooth surface. In the example PEG1500 (polyethylene glycol) dissolved to 1 wt. % in ethanol.

The cured layer on glass is used to test the protection. The cured layer on foil is pealed of and used upside down to test the release.

Figure 2:
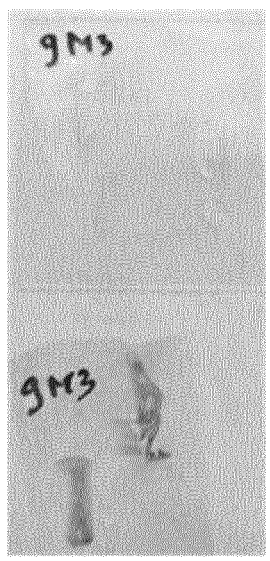
FIG. 2 is a photograph of test specimens of varnish layers.

A qualitative test is performed with a solution of KI, which in contact with HP turns brown due to the formation of $I_3^-$. This is shown in FIG. 2. Therein the glass substrate is at the top, while the foil is at the bottom.

The difference in the amount of peroxide released is evident from the presence or absence of colouring. It is shown that little peroxide is released from the cured film on the glass substrate. This means that the varnish composition of the invention is capable of retaining the peroxide. It is also shown that, on the hydrophilic foil, a substantial amount of peroxide has been released. Thus, the varnish composition of the invention serves to release peroxide where needed (viz. on a tooth surface) whilst retaining it to the extent not present on a hydrophilic surface.

The amount of peroxide released can be measured quantitatively with the Hannig assay, which is a known assay for peroxide release. Thereby the cured layer is contacted with a PBS solution (phosphate buffered saline), which is accepted in the art as a good representative material for saliva.

Figure 3:
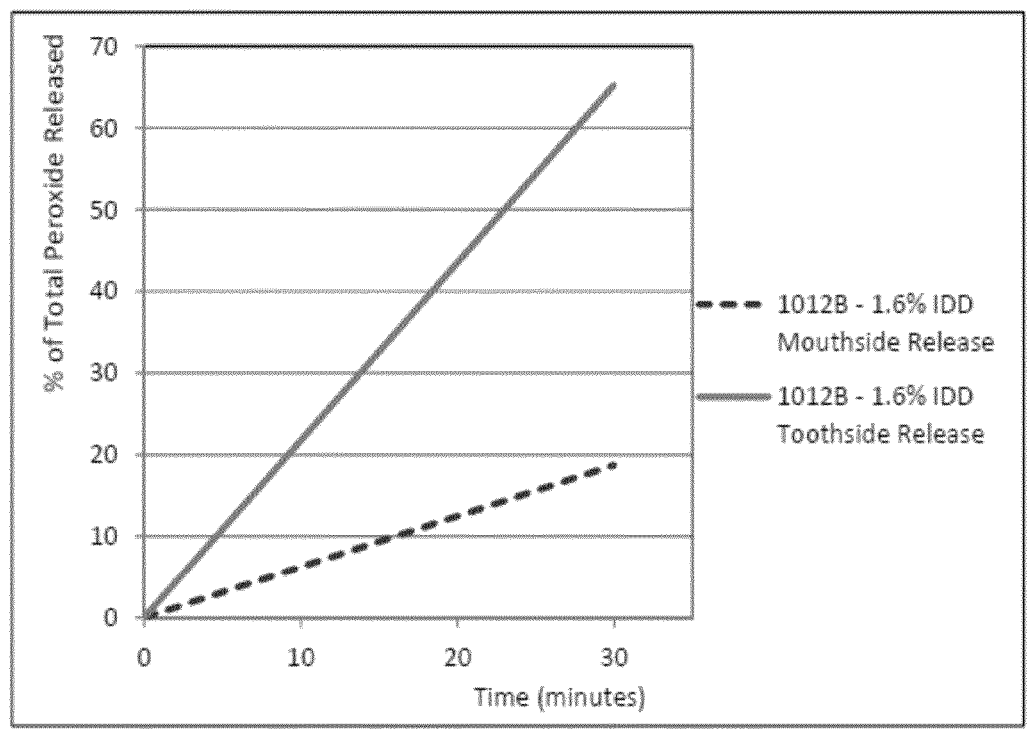
FIG. 3 is a graph depicting peroxide release in a test comparing tooth side release and mouth side release.

The results of another test for a single layer varnish composition of the invention (SLV) are shown in FIG. 3.

This test serves to assess the separation of the components of the SLV by monitoring the release of peroxide into solution (water, buffer) as a function of time. To assess release to the mouth; varnish is applied to a solid substrate and allowed to cure. Varnish and substrate are then immersed in a stirred solution and aliquots removed at timed intervals for peroxide concentration determination. To assess release to the tooth; varnish is again applied to a solid substrate and cured. The air-exposed surface of the varnish is then adhered to a piece of double-sided tape and peeled from the solid substrate on which it had been formed (exposing the surface that would normally be in contact with the tooth. This combination of tape and varnish is then attached to a second substrate (by virtue of the double-sided tape) which is then immersed and peroxide release determined as described above.

The graph in FIG. 3 shows that in a 30-minutes experiment, more peroxide was released from the tooth-side of the cured varnish (straight line) than from the mouth-side (dotted line), as is the intention of the formulation of the invention.

EXAMPLE 5

Preparation of Varnish Composition 2.25 grams of 50 wt % HP in water is emulsified in 1 wt. % solution of Span 83 in a mixture of 83 wt. % Isopar™ E and 17 wt. % isododecane using an Ultra Turrax®. Of this emulsion 2 grams is mixed with 0.5 grams of 20 wt. % Kraton G1643MS solution in Isopar™ E.

EXAMPLE 6

Whitening Tests

Whitening tests (extracted human testing) were conducted using two formulations of a single layer varnish according to the invention, compared with whitening obtained with strips (Crest White strips). The test involved nine times a 30-minute treatment (on human molars). Colour was assessed by recording L*a*b* values following a period of rehydration (6-hours or overnight). The rehydration in for the white strip experiments was done using a dampened tissue, in the varnish experiments by immersion in water.

Figure 4:
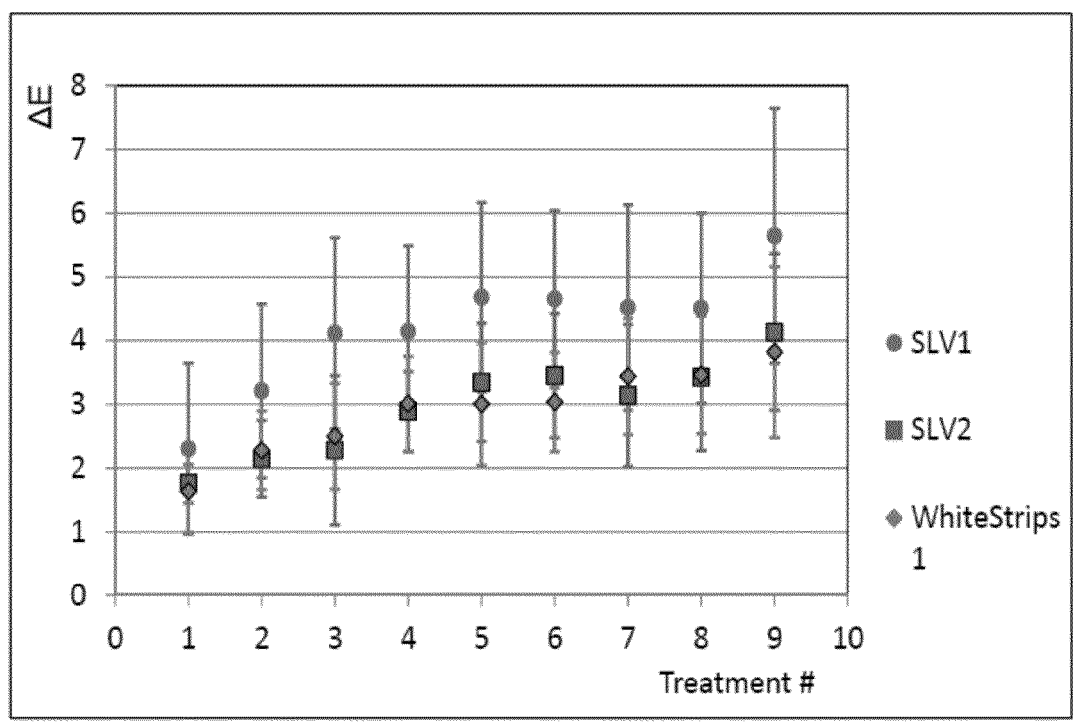
FIG. 4 is a graph depicting whitening results on extracted human teeth of a composition of the invention in comparison with the market standard.

The results are depicted in FIG. 4. Therein the two single layer varnish compositions of the invention are indicated by diamonds (SLV1) and squares (SLV2).

In FIG. 3 the Y-axis indicates the whitening effects in terms of a change in colour ($\Delta E$) and the X-axis indicates the number of treatment. The measurement points indicated by diamonds (♦) provide the results for the strips. The measurement points indicated by rounds (●) and squares (■) provide the results for, respectively, SLV1 and SLV2. As shown, the single layer varnish composition of the invention delivers equivalent whitening efficacy as the strips (SLV2) and better efficacy (SLV1).

The invention claimed is:

1. An oral care varnish composition comprising a dispersion of a hydrophilic oral care agent in a solution of a film-forming hydrophobic polymer in a non-polar solvent, wherein the polymer is selected from the group consisting of hydrogenated polyisobutene, Ethylene/Propylene/Styrene Copolymer, Butylene/Ethylene/Styrene Copolymer, alkylated polyvinylpyrrolidone, poly alpha olefins, Hydrogenated Polycyclopentadiene, Polyvinylstearylether, or polystyrene/rubber block-copolymers, and wherein the solvent is selected from the group consisting of pentane, isopentane, heptane, isooctane, isodecane, cyclomethicone (D4), cyclomethicone (D5), C7-9 isoparaffin, C8-9 isoparaffin, and mixtures of these solvents.

2. A varnish composition according to claim 1, wherein the dispersion is a suspension of hydrophilic particles comprising a solid peroxide.

3. A varnish composition according to claim 2, wherein the peroxide is selected from carbamide peroxide, PVP-hydrogen peroxide complexes, and mixtures thereof.

4. A varnish composition according to claim 1, wherein the dispersion is an emulsion of an aqueous solution of hydrogen peroxide.

5. A varnish composition according to claim 4, comprising at least one emulsifier.

6. A varnish composition according to claim 1, wherein the solvent is selected from the group consisting of heptane, isooctane, and mixtures thereof, optionally in admixture with isopentane or pentane.

7. An oral care varnish composition comprising a dispersion of a hydrophilic oral care agent in a solution of a film-forming hydrophobic polymer in a non-polar solvent, said solvent being volatile and being characterized as a better than theta $\theta$ solvent for the polymer, wherein the polymer is a linear triblock copolymer based on styrene and ethylene/butylene, and (SEBS), optionally grafted with maleic anhydride.

8. A varnish composition according to claim 1, wherein the dispersion comprises an oral care agent selected from the group consisting of sodium fluoride, ACP (amorphous calcium phosphate, including the calcium and phosphate precursors thereof), potassium nitrate, potassium oxalate, phosphates and polyphosphates, monofluorphosphate, aminfluoride, xylitol, chlorhexidine (CHX), cetylpyridiniumchloride (CPC), triclosan (Irgasan), stannous fluoride (SnF2), zinc acetate, silver diamine fluoride, hypochlorite, chlorine dioxide, and iodine.

9. A cured varnish composition on at least one tooth, obtainable by applying a varnish composition according to claim 1 on said at least one tooth, and curing said composition by evaporation of solvent, said cured composition comprising a hydrophilic oral care agent dispersed in a matrix of a hydrophobic polymer, wherein the hydrophilic oral care agent is present in an aggregate state at least at the surface of the cured composition facing the tooth, and a layer of the hydrophobic polymer is present at least the surface of the cured composition facing away from the tooth.

10. A method of applying an oral care agent to teeth, the method comprising providing a varnish composition as defined in claim 1 to at least one tooth, and allowing the solvent to evaporate so as to cure the varnish composition.

11. A method according to claim 10, wherein the oral care agent comprises a peroxide, the method being a teeth whitening method.

12. A method according to claim 10, wherein the oral care agent comprises an agent selected from the group consisting of sodium fluoride, ACP (amorphous calcium phosphate, including the calcium and phosphate precursors thereof), potassium nitrate, potassium oxalate, phosphates and polyphosphates, monofluorphosphate, aminfluoride, xylitol, chlorhexidine (CHX), cetylpyridiniumchloride (CPC), triclosan (Irgasan), stannous fluoride (SnF2), zinc acetate, silver diamine fluoride, hypochlorite, chlorine dioxide, and iodine.

13. A cosmetic method of whitening teeth of a subject, preferably a human subject, the method comprising applying a varnish composition according to claim 1 to at least one tooth of said subject, wherein the oral care agent comprises a peroxide, allowing the solvent to evaporate so as to form a cured varnish layer, and allowing the cured varnish layer to stay on said at least one tooth for a desired treatment period.

14. A cosmetic method according to claim 13, wherein the treatment period is of sufficient length so as to bring about a change in colour of at least 1 $\Delta E$, whereby $\Delta E$ is computed according to the formula:

$\Delta E = \sqrt{(L_2^* - L_1^*)^2 + (a_2^* - a_1^*)^2 + (b_2^* - b_1^*)^2}$, using the $L^*$, $a^*$, $b^*$ values of the teeth, with said values being CIE76 values according to the 1976 definition by the International Commission on Illumination, wherein the values denoted by the subscript 1 are before whitening, and, the values denoted by the subscript 2 are after whitening.

* * * * *